(12) United States Patent
Yuds et al.

(10) Patent No.: US 11,628,242 B2
(45) Date of Patent: Apr. 18, 2023

(54) SPENT DIALYSATE CONTAINER FOR DISPOSING SPENT DIALYSATE IN A DIALYSIS SYSTEM

(71) Applicant: Fresenius Medical Care Holdings, Inc., Waltham, MA (US)

(72) Inventors: David J. Yuds, Hudson, NH (US); Eric Bergman, Newton, MA (US); Jonathan F. Leclerc, Northborough, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 369 days.

(21) Appl. No.: 17/016,912

(22) Filed: Sep. 10, 2020

(65) Prior Publication Data

US 2022/0072208 A1     Mar. 10, 2022

(51) Int. Cl.
| | | |
|---|---|---|
| A61M 1/16 | (2006.01) | |
| A61M 1/28 | (2006.01) | |
| A61B 50/13 | (2016.01) | |
| A61M 1/00 | (2006.01) | |

(52) U.S. Cl.
CPC ........... *A61M 1/1668* (2014.02); *A61B 50/13* (2016.02); *A61M 1/1601* (2014.02);
(Continued)

(58) Field of Classification Search
CPC .. A61M 1/1601; A61M 1/1668; A61M 1/168; A61M 1/169; A61M 1/28;
(Continued)

(56) References Cited

U.S. PATENT DOCUMENTS

| | | |
|---|---|---|
| 4,229,299 A | 10/1980 | Savitz et al. |
| 4,412,917 A | 11/1983 | Ahjopalo |
| | (Continued) | |

FOREIGN PATENT DOCUMENTS

| | | |
|---|---|---|
| EP | 0112104 A2 | 6/1984 |
| EP | 0865794 A2 | 9/1998 |
| | (Continued) | |

OTHER PUBLICATIONS

International Search Report and Written Opinion for International application No. PCT/US2021/046841, dated Dec. 8, 2021, 13 pages.
(Continued)

*Primary Examiner* — John Kim
(74) *Attorney, Agent, or Firm* — KDW Firm PLLC (57) ABSTRACT

Dialysis systems for operating dialysis machines (e.g., peritoneal dialysis machines) for conducting dialysis treatments are disclosed. The dialysis system may include a spent dialysate container for receiving spent dialysate from a patient. In use, the spent dialysate containers are arranged and configured to provide one or more mechanical advantages to ease disposal of the spent dialysate. For example, the spent dialysate container may receive the spent dialysate from the patient and enable the patient or caregiver to dispose of the spent dialysate without requiring the patient or caregiver to lift bags of spent dialysate or incorporate lengthy drain lines. The spent dialysate container may include a reservoir to receive the spent dialysate, wheels to enable the patient or caregiver to transport the reservoir, mechanisms to facilitate disposal of the spent dialysate from the reservoir, a nozzle to dispose of the spent dialysate, and/or a disinfectant to disinfect the drain.

25 Claims, 8 Drawing Sheets

(52) U.S. Cl.
CPC ............ *A61M 1/168* (2013.01); *A61M 1/169* (2013.01); *A61M 1/28* (2013.01); *A61M 1/63* (2021.05); *A61M 2205/10* (2013.01); *A61M 2205/128* (2013.01); *A61M 2205/3553* (2013.01); *A61M 2209/08* (2013.01); *A61M 2209/10* (2013.01)

(58) Field of Classification Search
CPC ................ A61M 1/63; A61M 2205/10; A61M 2205/128; A61M 2205/3553; A61M 2209/08; A61M 2209/10; A61B 50/13
See application file for complete search history.

(56) References Cited

U.S. PATENT DOCUMENTS

| | | | |
|---|---|---|---|
| 6,217,328 | B1 | 4/2001 | Oliver |
| 2003/0164600 | A1 | 9/2003 | Dunn et al. |
| 2009/0187138 | A1 | 7/2009 | Lundtveit et al. |
| 2014/0343515 | A1 | 11/2014 | Sylvester et al. |
| 2016/0107128 | A1 | 4/2016 | Dumschat |
| 2016/0331876 | A1 | 11/2016 | Smith et al. |
| 2017/0028110 | A1 | 2/2017 | Smith et al. |
| 2018/0361033 | A1 | 12/2018 | Reasoner et al. |
| 2020/0254154 | A1 | 8/2020 | Reasoner et al. |

FOREIGN PATENT DOCUMENTS

| | | |
|---|---|---|
| GB | 2344858 A | 6/2000 |
| WO | 2021089690 A1 | 5/2021 |

OTHER PUBLICATIONS

Quantex™ Recyclable Pump Technology "How the Single-Use Pump Works", online [retrieved on Feb. 7, 2021]. Retrieved from Internet URL: https://www.quantex-arc.com/how-the-single-use-pump-works/, 5 pages.

SPENT DIALYSATE CONTAINER FOR DISPOSING SPENT DIALYSATE IN A DIALYSIS SYSTEM

FIELD OF THE DISCLOSURE

The disclosure generally relates to dialysis machines and systems, and more particularly to a dialysate container for receiving spent dialysate.

BACKGROUND

Dialysis machines are known for use in the treatment of renal disease. The two principal dialysis methods are hemodialysis (HD) and peritoneal dialysis (PD). During HD, the patient's blood is passed through a dialyzer of an HD machine while also passing dialysate through the dialyzer. A semi-permeable membrane in the dialyzer separates the blood from the dialysate within the dialyzer and allows diffusion and osmosis exchanges to take place between the dialysate and the blood stream. During PD, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. In Continuous Ambulatory Peritoneal Dialysis (CAPD), patients perform manual exchanges. Automated PD (APD) machines, called PD cyclers, are designed to control the entire PD process so that it can be performed at home, usually overnight, without clinical staff in attendance.

A dialysis machine, such as a PD machine, may include one or more containers (e.g., bags) containing a fluid (e.g., a dialysate) for patient infusion. In addition, a PD machine may include a removable and/or replaceable cartridge or cassette (used interchangeably without the intent to limit) attached to one or more fluid lines for pumping fluid to and from a patient. In PD machines, for example, one or more fluid lines are inserted into an abdomen of a patient for flowing fresh dialysate and removing used dialysate, waste, and excess fluid (collectively referred to herein as spent dialysis and/or spent dialysate without the intent to limit). As the cassette facilitates pumping of the fluid, the dialysis machine may monitor fluid delivery, fluid temperature, flow path, and pressure.

During a treatment operation, the dialysis machine pumps fluid, e.g., fresh and spent dialysate, to and from a patient. For example, the dialysis machine may pump dialysate from one or more dialysate bags and into the patient's abdomen. The dialysate may pass through a heating chamber to heat the dialysate to a predetermined temperature prior to inserting the dialysate into the machine. Next, the dialysis machine may remove the spent dialysate from the patient's abdomen. That is, after the dialysate has been inserted into the patient's abdomen and a prescribed amount of urea, creatine, water, and other waste matter (e.g., effluent) have been removed from the patient, the spent dialysate must be discarded.

Currently, spent dialysate may be connected, via a drain line or tube, to a drain or a drain bag. However, discarding spent dialysate into a drain or a drain bag presents one or more problems and/or inconveniences. For example, draining spent dialysate into a drain, which typically is in the form of a toilet, a sink, a tub, or the like, requires the dialysis treatment to be performed in relatively close proximity to the drain, which may not be ideal for the patient. In addition, and/or alternatively, the dialysis system may require a long drain line or tube that extends across the floor from the dialysis machine to the drain, potentially resulting in a tripping hazard. In addition, and/or alternatively, some patients may elect to install a drain into a treatment room. However, even if such installation is permissible, such installation may be costly. In the case of, for example, renters, such installation may be prohibited.

Dispensing of spent dialysate to one or more drain bags presents its own set of problems and inconveniences. For example, at the conclusion of the dialysis treatment, discarding spent dialysate into one or more drain bags requires the patient or caregiver to dispose of the relatively heavy drain bags. This may entail carrying the relatively heavy and cumbersome bags of spent dialysate to the drain. It is not uncommon for drain bags to weigh, depending on the patient size and prescription, between 13 and 22 pounds. Moreover, drain bags generally incorporate small openings for receiving the drain line. As a result, patients and caregivers have a tendency to cut open the drain bag to discard the spent dialysate more quickly. However, this increases the risk of accidental spillage.

In addition, in either event, discarding spent dialysate into a drain may require periodic cleaning of the drain to prevent dangerous biofilm buildup and/or replacing of the drain lines, which adds to the cost of the dialysis treatment. Utilization of long drain lines or tubing may also present additional inconveniences requiring the drain line to be secured (e.g., taped) to the floor to prevent, or at least minimize, tripping hazards.

With current options, some dialysis patients may be prevented from the benefit associated with home dialysis treatments due to the added costs associated with plumbing and/or physical requirements associated with carrying, lifting, and discarding the spent dialysate. Some patients may struggle to lift the drain bags or be subject to potential back strain or other injuries caused by handling the drain bags. Alternatively, for those who elect to use a drain line, the drain line can present a trip hazard in the event that the drain line is not properly secured. Even if properly secured, long drain lines may present additional costs, inconveniences, and an unaesthetic eyesight to one's home.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a spent dialysate container is disclosed. In one embodiment, the spent dialysate container comprises a reservoir arranged and configured to receive spent dialysate resulting from a dialysis treatment, wheels arranged and configured to enable the spent dialysate container to move, and a pump arranged and configured to evacuate the spent dialysate from the reservoir to facilitate disposal of the spent dialysate.

In one embodiment, the pump comprises a plate pivotably coupled to a base of the spent dialysate container, the plate movable from a first position to a second position, in the second position, the plate compresses the reservoir causing the spent dialysate to evacuate the reservoir.

In one embodiment, the spent dialysis container further comprises a lever arranged and configured to move the plate between the first and second positions.

In one embodiment, one or more of the wheels are motorized to facilitate motorized movement of the spent dialysate container.

In one embodiment, the motorized movement of the spent dialysate container is controllable by one or more of (i) controls disposed on the spent dialysate container, or (ii) a remote controller.

In one embodiment, the spent dialysate container further comprises one or more sensors arranged and configured to enable the spent dialysate container to autonomously move to a designated drain for permanent disposal of the spent dialysate.

In one embodiment, the spent dialysate container further comprises a flexible hose and a nozzle at an end thereof for evacuating the spent dialysate from the reservoir and an extendable arm operatively coupled to the nozzle, the extendable arm movable between a first, folded position and a second extended position, in the second position, the extendable arm facilitating placement of the nozzle relative to a drain.

In one embodiment, the spent dialysate container further comprises a motor for moving the extendable arm between the first and second positions, wherein the motor is arranged and configured to automatically move the extendable arm from the first position to the second position when one or more sensors detect that the spent dialysate container is positioned adjacent to the drain.

In one embodiment, the pump is arranged and configured to automatically evacuate the spent dialysate when one or more sensors detect that the spent dialysate container is positioned adjacent to the drain.

In one embodiment, the spent dialysate container further comprises a container for storing a disinfectant and a valve, the valve configurable between an opened position and a closed position, in the opened position, the container releasing disinfectant to clean a drain, the reservoir, or a combination thereof.

According to another exemplary embodiment of the present disclosure, a dialysis system for conducting a dialysis treatment is disclosed. The dialysis system comprising a dialysate source for use in the dialysis treatment, a dialysis machine for transferring dialysate from the dialysate source during the dialysis treatment, and a spent dialysate container for receiving spent dialysate resulting from the dialysis treatment via the dialysis machine. In one embodiment, the spent dialysate container includes a reservoir arranged and configured to receive the spent dialysate, wheels arranged and configured to enable the spent dialysate container to move, and a pump arranged and configured to evacuate the spent dialysate from the reservoir to facilitate disposal of the spent dialysate.

In one embodiment, the spent dialysate container further comprises a plate pivotably coupled to a base of the spent dialysate container, the plate movable from a first position to a second position, in the second position, the plate compresses the reservoir causing the spent dialysate to evacuate the reservoir.

In one embodiment, the spent dialysate container further comprises a lever arranged and configured to move the plate between the first and second positions.

In one embodiment, one or more of the wheels are motorized to facilitate motorized movement of the spent dialysate container.

In one embodiment, the movement of the spent dialysate container is controllable by one or more of (i) controls disposed on the spent dialysate container, or (ii) a remote controller.

In one embodiment, the spent dialysate container includes one or more sensors arranged and configured to enable the spent dialysate container to autonomously move to a designated drain for permanent disposal of the spent dialysate.

In one embodiment, the spent dialysate container includes a flexible hose and a nozzle at an end thereof for evacuating the spent dialysate from the reservoir, the spent dialysate container further including an extendable arm operatively coupled to the nozzle, the extendable arm movable between a first, folded position and a second extended position, in the second position, the extendable arm facilitating placement of the nozzle relative to a drain.

In one embodiment, the spent dialysate container further comprises a motor for moving the extendable arm between the first and second positions, wherein the motor is arranged and configured to automatically move the extendable arm from the first position to the second position when one or more sensors detect that the spent dialysate container is positioned adjacent to the drain.

In one embodiment, the pump is arranged and configured to automatically evacuate the spent dialysate when one or more sensors detect that the spent dialysate container is positioned adjacent to the drain.

In one embodiment, the spent dialysate container further comprises a container for storing a disinfectant and a valve, the valve configurable between an opened position and a closed position, in the opened position, the container releasing disinfectant to clean a drain, the reservoir, or a combination thereof.

BRIEF DESCRIPTION OF THE DRAWINGS

By way of example, specific embodiments of the disclosed methods and devices will now be described, with reference to the accompanying drawings, in which.

DETAILED DESCRIPTION

The present embodiments will now be described more fully hereinafter with reference to the accompanying drawings, in which several exemplary embodiments are shown. The subject matter of the present disclosure, however, may be embodied in many different forms and types of devices and systems for dialysis systems and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of an improved guided user-unencumbered septic evacuator (GUUSE) or spent dialysate container (used interchangeably herein without the intent to limit) for receiving spent dialysate from a patient is disclosed herein. In use, the spent dialysate containers are arranged and configured to be used with dialysis machines or in dialysis systems. In accordance with one or more aspects of the present disclosure, a spent dialysate container may be connected to a dialysis machine via, for example, tubing, for receiving spent dialysate from a patient, the spent dialysate to be temporarily stored in the spent dialysate container until the spent dialysate can be permanently disposed within, for example, a drain such as, for example, a toilet, a tub, a sink, etc. In use, the spent dialysate containers are arranged and configured to provide one or more mechanical advantages to ease disposal of the spent dialysate. For example, the spent dialysate container may be arranged and configured to receive the spent dialysate from the patient and enable the patient or caregiver to dispose of (e.g., drain) the spent dialysate without requiring the patient or caregiver to lift the bags or incorporate lengthy drain lines.

In accordance with one or more aspects of the present disclosure, the spent dialysate container may include one or more features selected from, for example, a reservoir arranged and configured to receive the spent dialysate from the patient, wheels to enable the patient or caregiver to easily move the spent dialysate container without requiring the patient or caregiver to carry the bags of spent dialysate and/or without the need for lengthy drain tubing, one or more mechanisms to facilitate disposal (e.g., removal) of the spent dialysate from the reservoir, a nozzle and/or hose to facilitate placement and/or disposal of the spent dialysate, and/or a disinfectant for facilitating disinfecting of the drain and/or spent dialysate container.

In one embodiment, the reservoir may be in the form of a non-rigid bag. The spent dialysate container may include a bellows for dispensing spent dialysate from the bag. Alternatively, in another embodiment, the reservoir may be rigid. The spent dialysate container may include a pump for dispensing the spent dialysate from the reservoir. In addition, and/or alternatively, in one embodiment, the spent dialysate container may be automated to facilitate motorized and/or self-driving of the spent dialysate container, and/or self-dispensing of the spent dialysate from the reservoir.

While the spent dialysate container will be shown and described in the present disclosure for use with one or more dialysis machines, it should be appreciated that the spent dialysate container should not be limited to any particular type of dialysis machine. It is envisioned that the spent dialysate container according to one or more aspects of the present disclosure may be used in connection with other types of dialysis machines. Thus, the present disclosure should not be limited to any particular type of dialysis machine unless specifically claimed.

Figure 1:
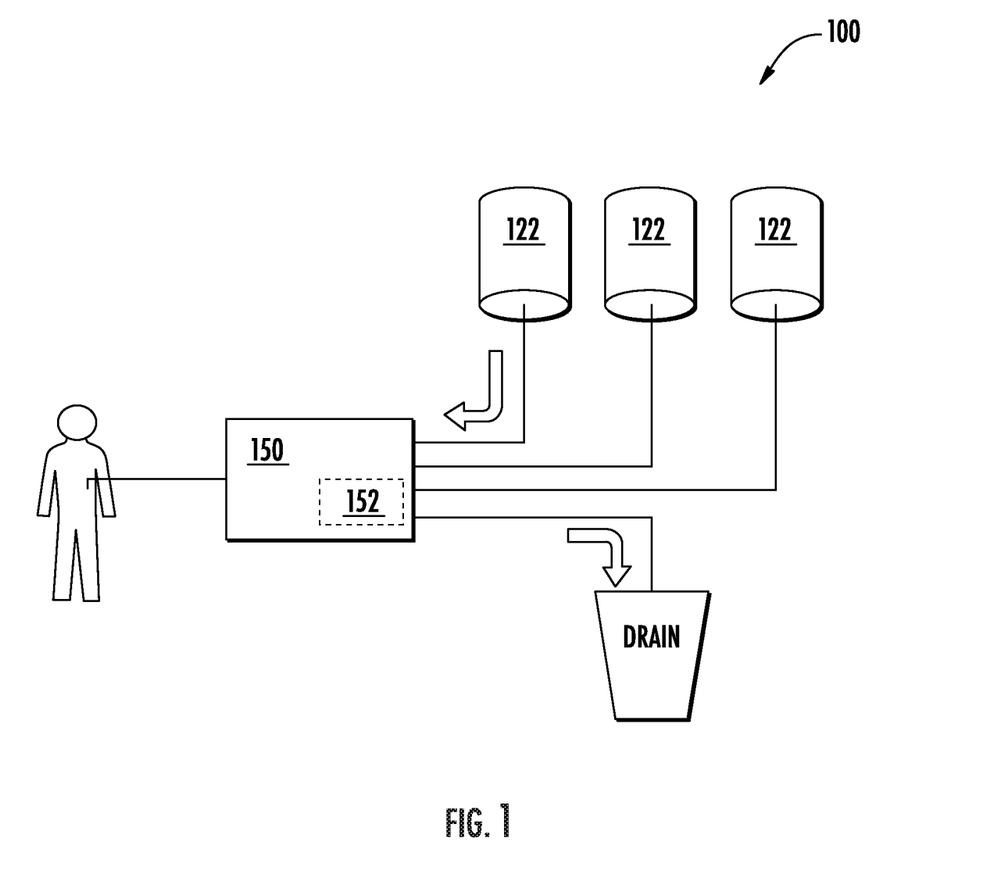
FIG. 1 illustrates an example of an embodiment of a dialysis system.

Referring to FIG. 1, a dialysis system 100 may include a PD machine 150, for flowing fresh dialysate into a patient and draining spent dialysate out of the patient. During treatment, a volume of dialysate may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the spent dialysate may be flowed out of the patient's abdomen and purged to a drain connected to the tubing, e.g., the drain line. This exchange of fresh dialysate and spent dialysate after a dwell time may occur for several cycles depending on the patient's treatment regimen.

One or more dialysate sources may be connected to the dialysis machine 150. In some embodiments, as illustrated, the dialysate source(s) may be dialysate bags 122 that are hung near the PD machine 150 which may improve air content management as any air content is disposed by gravity to a top portion of the dialysate bag 122. Valves may be attached to a bottom portion of the dialysate bags 122 so fluid is drawn out and air content delivery is minimized. In one embodiment, as shown, dialysate from the dialysate bags 122 may be transferred directly to the patient through a warmer pouch, a heating chamber, or the like 152 (used interchangeably without the intent to limit) formed in the dialysis machine 150. When the dialysate has reached a predetermined temperature (e.g., approximately 98°-100° F., 37° C.) in the heating chamber 152, the dialysate may be flowed into the patient. As will be described and illustrated in greater detail below, the dialysate bags 122 may be connected to a cartridge or cassette (used interchangeably without the intent to limit), which may be insertable into the dialysis machine 150. In use, the cassette may be connected to dialysate bag lines, which may be used to pass dialysate from dialysate bags 122 to the cassette. In use, the cassette may be disposable. Alternatively, the cassette may be reusable. In addition, a patient line and a drain line may be connected to the cassette. The patient line may be connected to a patient's abdomen via a catheter and may be used to pass dialysate back and forth between the cassette and the patient's peritoneal cavity during use. The drain line may be connected to a drain or drain receptacle and may be used to pass dialysate from the cassette to the drain or drain receptacle during use. Although the system described herein is discussed principally in connection with the use of dialysate bags as the dialysate source, it is noted that, in other embodiments, different dialysate sources may be used. For example, in other embodiments, the dialysate source may include one or more containers in which dialysate is mixed and/or otherwise prepared at the PD machine from a dialysate concentrate, see, e.g., U.S. Pat. No. 10,076,599 to Eyrard et al., entitled "Dry Peritoneal Dialysis Concentrate System," which is incorporated by reference herein in its entirety.

Figure 2:
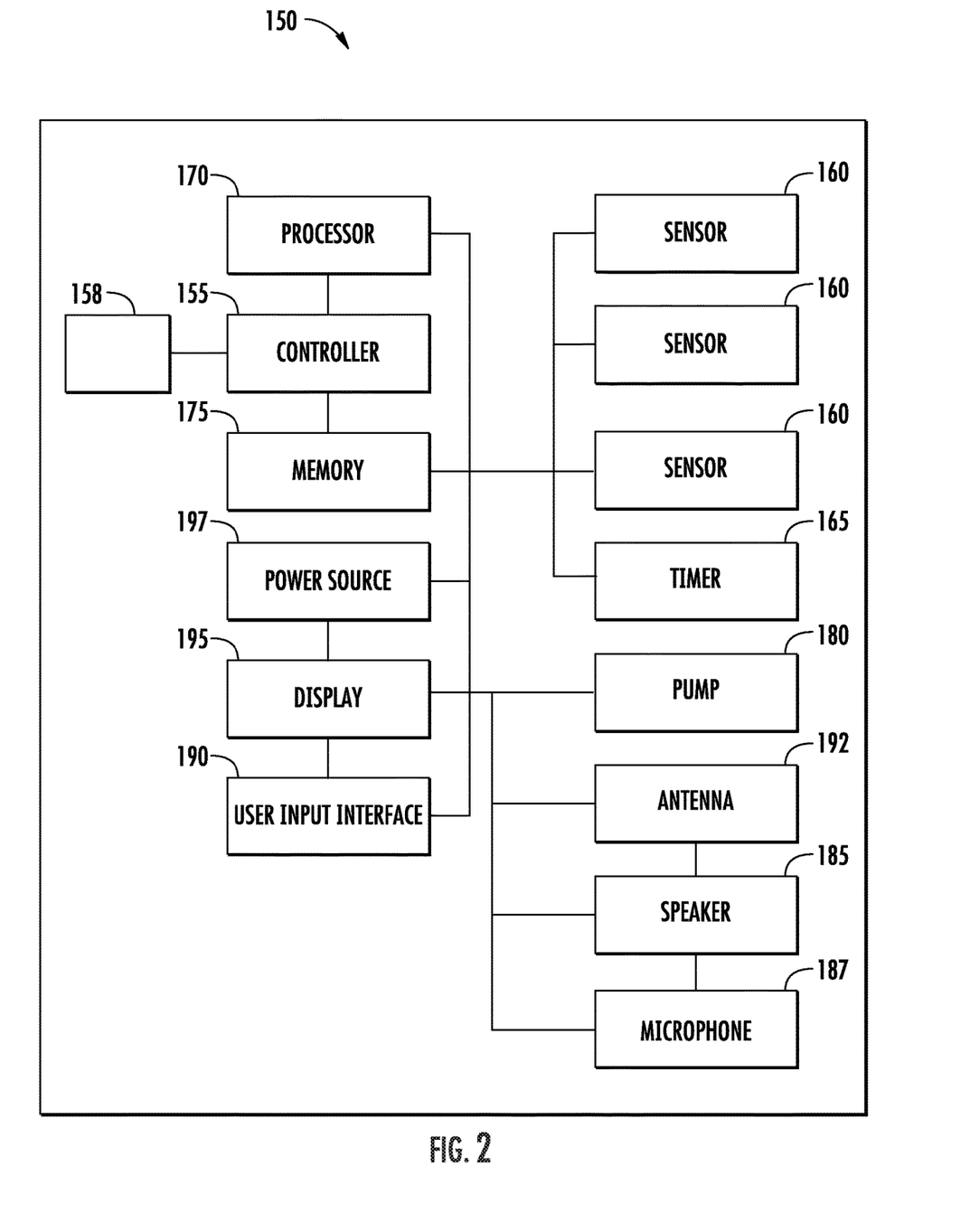
FIG. 2 is a block diagram illustrating an example of an embodiment of a dialysis machine that can be used in the dialysis system of FIG. 1.

Referring to FIG. 2, a schematic of an exemplary embodiment of a dialysis machine such as, for example, dialysis machine 150 is shown. The dialysis machine 150 may be a home dialysis machine, e.g., a PD machine, for performing a dialysis treatment on a patient, and may be included in the system 100 described above with respect to FIG. 1. In use, the dialysis machine 150 may include a controller 155 disposed in the dialysis machine 150. Alternatively, the dialysis machine 150 may be coupled to the controller 155, or other external systems, via a communication port or wireless communication links. The controller 155 may automatically control execution of a treatment function during a course of dialysis treatment.

The controller 155 may be operatively connected to the sensors 160 and deliver a signal to execute a treatment function (e.g., transferring dialysate from the dialysate bag 122 through the heating chamber 152 and then to the patient), or a course of treatment associated with various treatment systems. In some embodiments, a timer 165 may be included for timing the triggering of the sensors 160. The controller 155 may communicate control signals or triggering voltages to the components of the dialysis machine 150, and may include wireless communication interfaces. The controller 155 may detect remote devices to determine if any remote sensors are available to augment any sensor data being used to evaluate the patient. For example, remote devices may include smart phone microphones, video cameras, cameras, thermal imaging cameras, in bed sensors, sleep manager applications and sensors, web cameras, fitness sensors, stand-alone sensors, and the like.

In some embodiments, the machine 150 may also include a processor 170, a memory 175, and/or the controller 155, or combinations thereof and/or the machine 150 may receive signals from the sensor(s) 160 indicating various parameters. Each fluid bag (e.g., the dialysate bags 122) may contain an approximate amount of dialysate, such that "approximate amount" may be defined as a 3 L fluid bag containing 3000 to 3150 mL, a 5 L fluid bag containing 5000 to 5250 mL, and a 6 L fluid bag containing 6000 to 6300 mL. The controller 155 may also detect connection of all fluid bags 122 connected.

Communication between the controller 155 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In some embodiments, as will be described in greater detail below, the dialysis machine 150 may include at least one pump 180 operatively connected to the controller 155. During a treatment operation, the controller 155 may control the pump 180 for pumping fluid, e.g., fresh and spent dialysate, to and from a patient. The pump 180 may also pump dialysate from the dialysate bag 122 through, for example, the heating chamber 152.

The dialysis machine 150 may also include a user input interface 190, which may include a combination of hardware and software components that allow the controller 155 to communicate with an external entity, such as a patient or other user. These components may be configured to receive information from actions such as physical movement or gestures and verbal intonation. In some embodiments, the components of the user input interface 190 may provide information to external entities. Examples of the components that may be employed within the user input interface 190 include keypads, buttons, microphones, touch screens, gesture recognition devices, display screens, and speakers. The dialysis machine 150 may also include a display 195 and a power source 197.

In some embodiment, the user interface 190 and display 195 may be, for example, a touch screen and a control panel operable by a user (e.g., a caregiver or a patient) to allow, for example, set up, initiation, and/or termination of a dialysis treatment. The touch screen and the control panel may allow an operator to input various treatment parameters to the dialysis machine and to otherwise control the dialysis machine. In addition, the touch screen may serve as the display. The touch screen may function to provide information to the patient and/or the operator of the dialysis system. For example, the touch screen may display information related to a dialysis treatment to be applied to the patient, including information related to a prescription. The touch screen and/or display may include one or more buttons for selecting and/or entering user information.

The dialysis machine 150 may also be connectable for remote communication. For example, the dialysis machine 150 may be configured to connect to a network. The connection to network may be via a wired and/or wireless connection. In one embodiment, the dialysis machine 150 includes, for example, an antenna or other connection component 192 to facilitate connection to a network. The antenna 192 may be, for example, a transceiver for wireless connections and/or other signal processor for processing signals transmitted and received. Other medical devices (e.g., other dialysis machines) or components may be configured to connect to the network and communicate with the dialysis machine 150.

The dialysis machine 150 may also include a speaker 185 and a microphone 187. The controller 155 being operatively connected to the speaker 185 and the microphone 187.

As shown in FIG. 2, the sensors 160 may be included for monitoring parameters and may be operatively connected to at least the controller 155, the processor 170, and/or the memory 175, or combinations thereof. The processor 170 may be configured to execute an operating system, which may provide platform services to application software, e.g., for operating the dialysis machine 150. These platform services may include inter-process and network communication, file system management and standard database manipulation. One or more of many operating systems may be used, and examples are not limited to any particular operating system or operating system characteristic. In some examples, the processor 170 may be configured to execute a real-time operating system (RTOS), such as RTLinux, or a non-real time operating system, such as BSD or GNU/Linux.

In one embodiment, the processor 170 is arranged and configured to communicate with the user interface (e.g., touch screen and control panel). The processor 170 may be configured to receive data from the user interface 190 (e.g., touch screen, control panel), sensors such as, for example, weight, air content, flow, temperature, and/or pressure sensors, and control the dialysis machine 150 based on the received data. For example, the processor 170 may adjust the operating parameters of the dialysis machine 150. According to a variety of examples, the processor 170 may be a commercially available processor such as a processor manufactured by INTEL, AMD, MOTOROLA, and FREESCALE. However, the processor 170 may be any type of processor, multiprocessor or controller, whether commercially available or specially manufactured. For instance, according to one example, the processor 170 may include an MPC823 microprocessor manufactured by MOTOROLA.

The memory 175 may include a computer readable and writeable nonvolatile data storage medium configured to store non-transitory instructions and data. In addition, the memory 175 may include a processor memory that stores data during operation of the processor 170. In some examples, the processor memory includes a relatively high performance, volatile, random access memory such as dynamic random-access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 175 may include executable programs or other code that may be executed by the processor 170. The instructions may be persistently stored as encoded signals, and the instructions may cause the processor 170 to perform the functions described herein. The memory 175 may include information that is recorded, on or in, the medium, and this information may be processed by the processor 170 during execution of instructions. The memory 175 may also include, for example, specification of data records for user timing requirements, timing for treatment and/or operations, historic sensor information, and the like. The medium may, for example, be optical disk, magnetic disk or flash memory, among others, and may be permanently affixed to, or removable from, the controller 155.

The sensor(s) 160 may include a pressure sensor for monitoring fluid pressure of the machine 150, although the sensors 160 may also include any of a heart rate sensor, a respiration sensor, a temperature sensor, a weight sensor, an air sensor, a video sensor, a thermal imaging sensor, an electroencephalogram sensor, a motion sensor, an audio sensor, an accelerometer, a capacitance sensor, or any other suitable sensor. It is appreciated that the sensors 160 may include sensors with varying sampling rates, including wireless sensors.

The controller 155 may be disposed in the dialysis machine 150 or may be coupled to the dialysis machine 150 via a communication port or wireless communication links, shown schematically as communication element 158. According to various examples, the communication element 158 may support a variety of one or more standards and protocols, examples of which include USB, Wi-Fi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 150, the controller 155 may be operatively connected to any of the sensors 160, the pump 180, and the like. The controller 155 may communicate control signals or triggering voltages to the components of the machine 150. As discussed, exemplary embodiments of the controller 155 may include wireless communication interfaces. The controller 155 may detect remote devices to determine if any remote sensors are available to augment any sensor data being used to evaluate the patient.

Figure 3A:
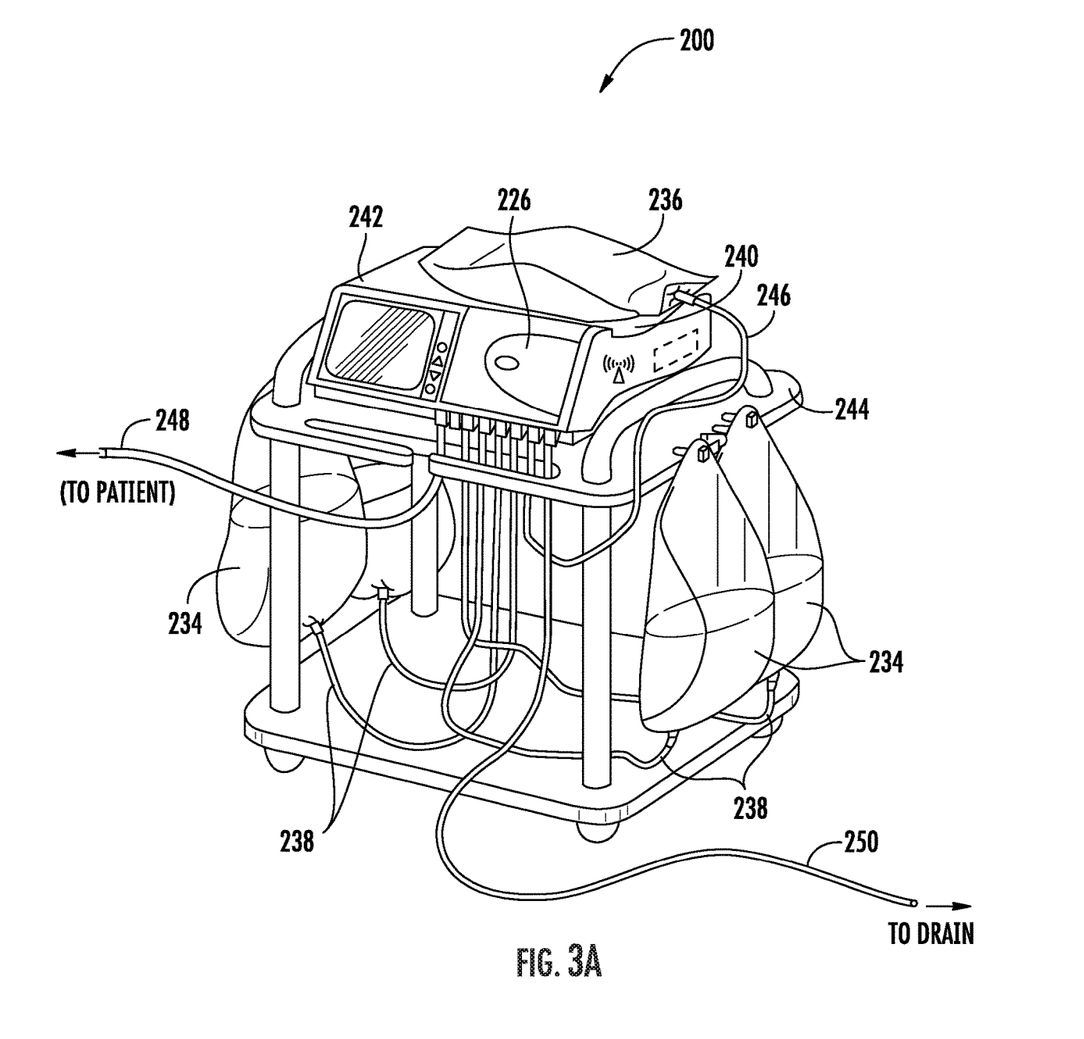
FIGS. 3A and 3B illustrate an example of an embodiment of a dialysis machine that can be used in the dialysis system of FIG. 1.
Figure 3B:
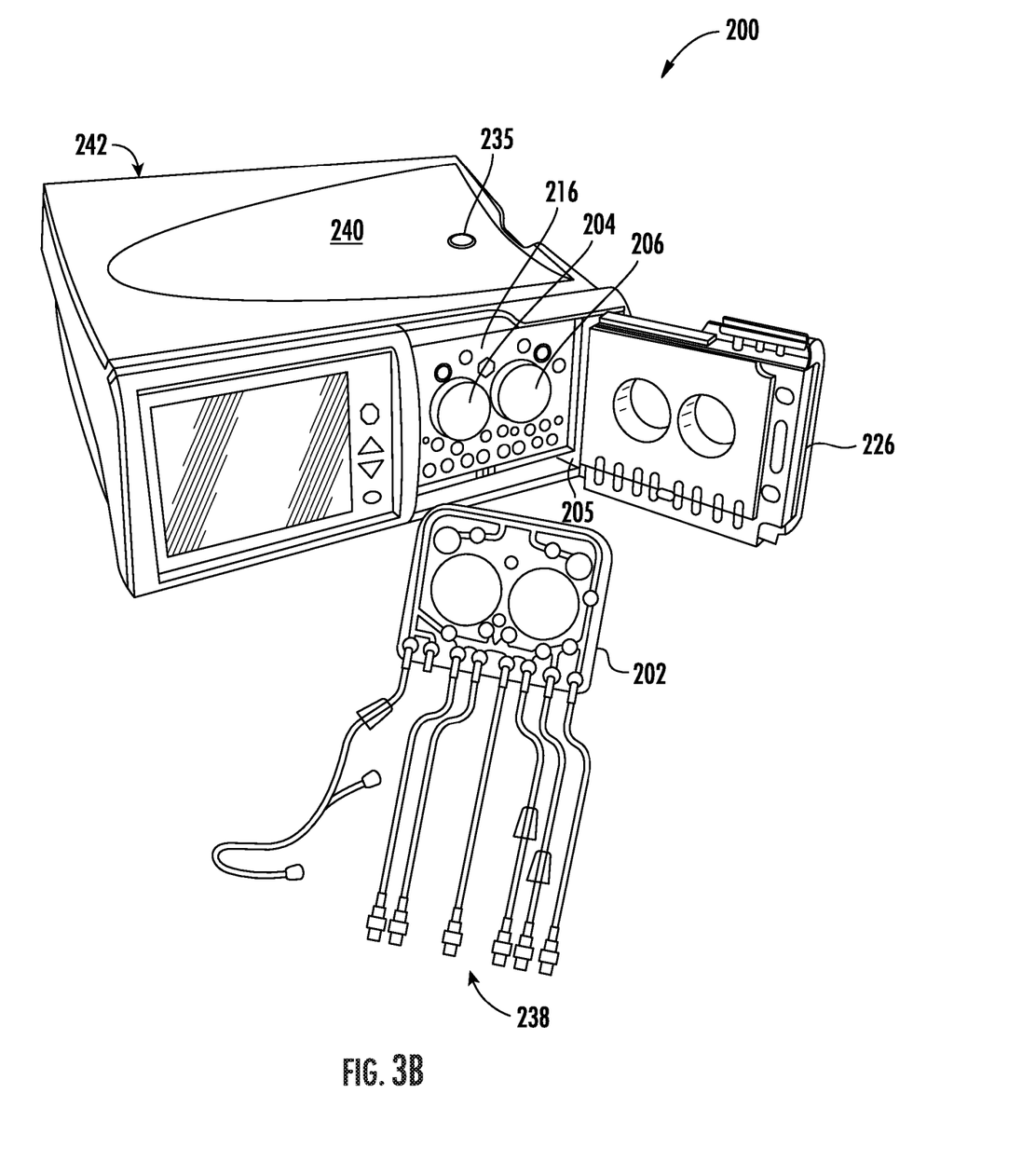

Referring now to FIGS. 3A and 3B, an example of an embodiment of a dialysis machine 200 such as, for example, dialysis machine 150, that can be used in connection with the dialysis system 100 shown in FIG. 1 is illustrated. The dialysis machine 200 may include the components described above with respect to the schematic of the system 100 and the machine 150 illustrated in FIGS. 1 and 2. The dialysis machine 200 may be configured to provide home dialysis treatment, for example, PD. In some implementations, the dialysis system and machine may be a home PD system, e.g., a PD system configured for use at a patient's home.

The dialysis machine 200 may include a housing 242, a door 226, and a cassette interface including piston or pump heads 204, 206 (used interchangeably herein without the intent to limit) for contacting a cartridge or cassette 202 (used interchangeably without the intent to limit), where the cassette 202 is located within a compartment formed between the cassette interface and the closed door 226 (e.g., cavity 205). Fluid lines (e.g., tubing) may be coupled to the cassette 202 in a known manner, such as via a connector, and may further include valves for controlling fluid flow to and from fluid bags including fresh dialysate and warming pouch. In some embodiments, when a cassette 202 is incorporated, at least a portion of the fluid lines (e.g., tubing) may be integral to the cassette 202. Prior to operation, a user may open the door 226 to insert a fresh cassette 202 and to remove the used cassette 202 after operation.

The cassette 202 may be placed in the cavity 205 of the machine 200 for operation. The machine 200 may manage flowing dialysate into a patient's abdomen, and removal of the spent dialysate and waste after a predetermined amount of time. During operation, dialysate fluid may be flowed into a patient's abdomen via the cassette 202, and spent dialysate, waste, and/or excess fluid may be removed from the patient's abdomen via the cassette 202. In some embodiments, a cassette pump plate 216 may be provided, which may contain a pump mechanism and provide openings for the pump heads 204, 206 to operate on an inserted cassette 202.

While the dialysate is present in a peritoneal cavity of the patient, the dialysate may absorb contaminants and/or particulates from the patient's blood. PD uses the patient's peritoneum in the abdomen as a membrane across which fluids and dissolved substances (e.g., electrolytes, urea, glucose, albumin, osmotically active particles, and other small molecules) are exchanged from the blood. PD for a patient may include a total treatment of approximately 10 to 30 liters of fluid, where approximately 2 liters of dialysate fluid are pumped into a patient's abdomen, held for a period of time, e.g., about an hour, and then pumped out of the patient. This is repeated until the full treatment volume is achieved, and usually occurs overnight while a patient sleeps.

The machine 200 may operate the pump heads 204, 206 to move the fluid. The pump heads 204, 206 apply force to the cassette 202, that connect a fluid reservoir, e.g., dialysate bags to a catheter at the patient's peritoneum. By operation of the pump heads 204, 206, fresh dialysate may be introduced into the patient's peritoneum. Likewise, the pump heads 204, 206 may draw fluid from the patient's peritoneum into a fluid reservoir (e.g., bag) or drain to waste. Multiple dialysate bags may be used including a clean fluid reservoir and a waste fluid reservoir. Operation of the pump heads 204, 206 in conjunction with valves controls delivery or retrieval of fluid.

In connection with PD machine 200, the heating element 152 may be in the form of a heater tray 240 including a heating element 235 positioned, for example, on top of the housing 242 of the machine 200. The heater tray 240 may be any size and shape to accommodate a bag of dialysate (e.g., a 5 L bag of dialysate) for batch heating. In use, for example, dialysate bags 234 may be suspended from hooks on the sides of a cart 244, and a heater bag 236 may be positioned in the heater tray 240. Connectors and tubing ports may connect the dialysate bags 234 and lines for transferring dialysate. Dialysate from the dialysate bags 234 may be transferred to the heater bag 236 in batches. For example, a batch of dialysate may be transferred from one or more dialysate bags 234 to the heater bag 236, where the dialysate is heated by the heating element 235. When the batch of dialysate has reached a predetermined temperature (e.g., approximately 98°-100° F., 37° C.), the batch of dialysate may be flowed into the patient. The dialysate bags 234 and the heater bag 236 may be connected to the cassette 202 via dialysate bag lines or tubing 238 and a heater bag line or tubing 238, respectively. The dialysate bag lines 238 may be used to pass dialysate from dialysate bags 234 to the cassette 202 during use, and a heater bag line 246 may be used to pass dialysate back and forth between the cassette 202 and the heater bag 236 during use. In addition, a patient line 248 and a drain line 250 may be connected to the cassette 202. The patient line 248 may be connected to a patient's abdomen via a catheter and may be used to pass dialysate back and forth between the cassette 202 and the patient's peritoneal cavity by the pump heads 204, 206 during use. The drain line 250 may be connected to a drain or drain receptacle and may be used to pass dialysate from the cassette 202 to the drain or drain receptacle during use.

Figure 4A:
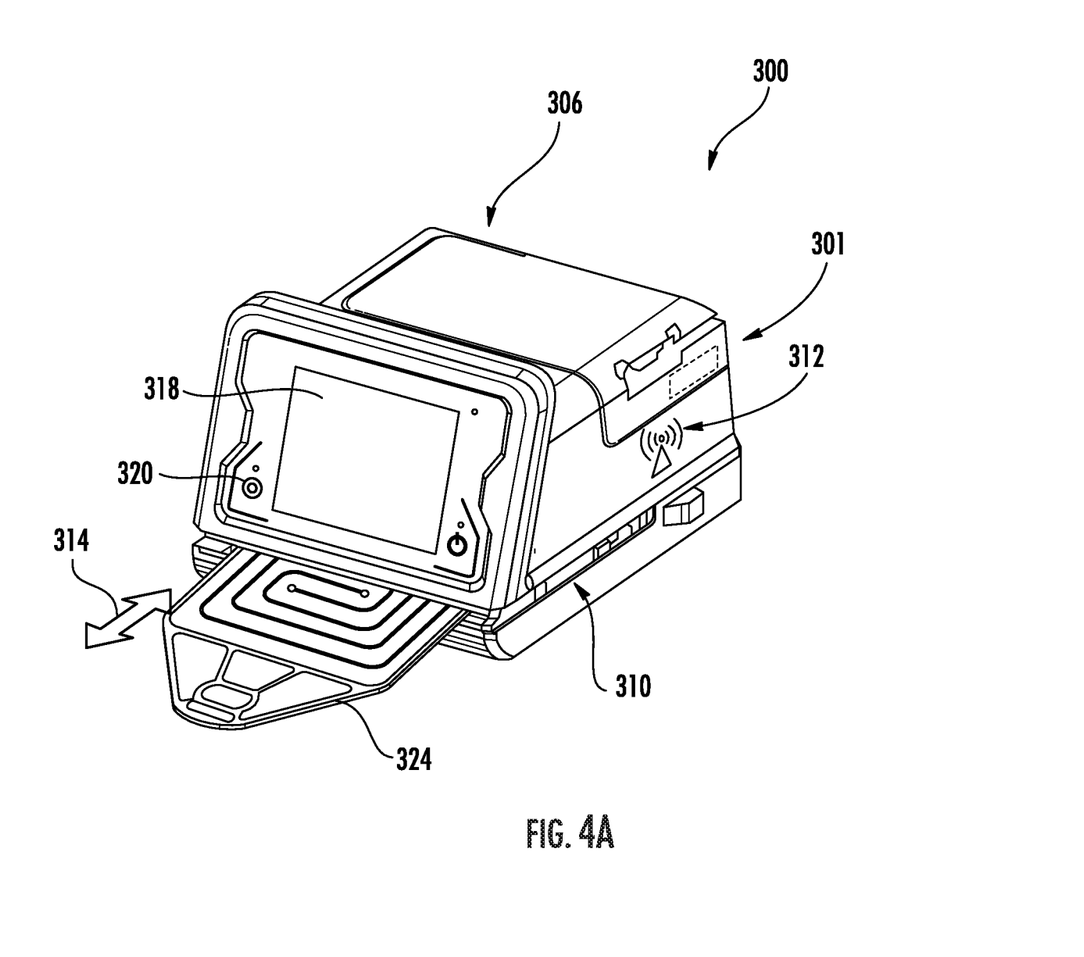
FIGS. 4A and 4B illustrate an example of an embodiment of a dialysis machine that can be used in the dialysis system of FIG. 1.
Figure 4B:
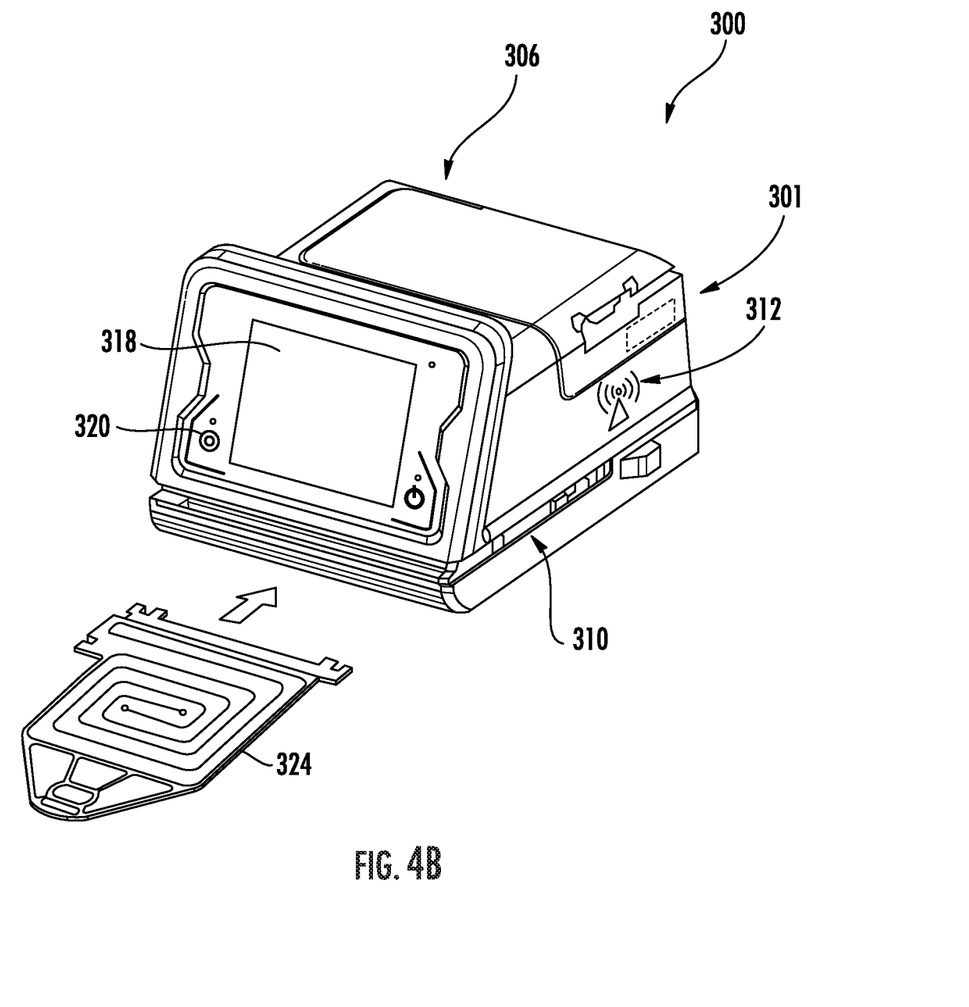

Referring to FIGS. 4A and 4B, an alternate example of an embodiment of a dialysis machine 300 such as, for example, dialysis machine 150, that can be used in connection with the dialysis system 100 shown in FIG. 1 is illustrated. The dialysis machine 300 may include the components described above with respect to the schematic of the system 100 and the machine 150 illustrated in FIGS. 1 and 2. The dialysis machine 300 may be configured to provide home dialysis treatment, for example, PD. In some implementations, the dialysis system and machine may be a home PD system, e.g., a PD system configured for use at a patient's home.

As illustrated, the dialysis machine 300 may be implemented in the dialysis system 100 and may include, for example, a housing 306, a processing module 301, a connection component 312, a touch screen 318, and a control panel 320 operable by a user (e.g., a caregiver or a patient) to allow, for example, set up, initiation, and/or termination of a dialysis treatment.

The touch screen 318 and the control panel 320 may allow a user to input various treatment parameters to the dialysis machine 300 and to otherwise control the dialysis machine 300. In addition, the touch screen 318 may serve as a display. The touch screen 318 may function to provide information to the patient and the operator of the dialysis system 100. For example, the touch screen 318 may display information related to a dialysis treatment to be applied to the patient, including information related to a prescription.

The dialysis machine 300 may include a processing module 301 that resides inside the dialysis machine 300, the processing module 301 being configured to communicate with the touch screen 318 and the control panel 320. The processing module 301 may be configured to receive data from the touch screen 318, the control panel 320, and sensors, e.g., air, temperature and pressure sensors, and control the dialysis machine 300 based on the received data. For example, the processing module 301 may adjust the operating parameters of the dialysis machine 300. In some embodiments, the processing module 301 may be an MPC823 PowerPC device manufactured by Motorola, Inc.

The dialysis machine 300 may be configured to connect to a network. The connection to network may be via a wired and/or wireless connection. The dialysis machine 300 may include a connection component 312 configured to facilitate the connection to the network. The connection component 312 may be a transceiver for wireless connections and/or other signal processor for processing signals transmitted and received over a wired connection. Other medical devices (e.g., other dialysis machines) or components may be configured to connect to the network and communicate with the dialysis machine 300.

In connection with the dialysis machine 300, one or more heating elements may be disposed internal to the dialysis machine 100. For example, a warmer pouch 324 may be insertable into an opening 310 in a direction indicated at arrow 314. It is also understood that the warmer pouch 324 may be connectable to the dialysis machine 300 via tubing, or fluid lines, via a cartridge. The tubing may be connectable so that dialysate may flow from containers (e.g., dialysate bags), through the warmer pouch 324 for heating, and to the patient.

In such in-line heating embodiments, the warmer pouch 324 may be configured so dialysate may continually flow through the warmer pouch 324 to achieve a predetermined temperature before flowing into the patient. Internal heating elements (not shown) may be positioned above and/or below the opening 310, so that when the warmer pouch 324 is inserted into the opening 310, the one or more heating elements may affect the temperature of dialysate flowing through the warmer pouch 324. In some embodiments, the internal warmer pouch may instead be a portion of tubing in the system that is passed by, around, or otherwise configured with respect to, a heating element(s). It is understood that FIGS. 4A and 4B illustrate dialysate continuously flowing through the warmer pouch 324 "in-line" with the dialysis machine 300, reaching an acceptable temperature by the application of internal heating elements, and that FIGS. 3A and 3B, as described above, illustrate that dialysate may be transferable to and stored in the heater bag 236 by "batch" until reaching an acceptable temperature for use.

In embodiments, a patient line may be connected to the cartridge. The patient line may be connectable to a patient's abdomen (e.g., peritoneal cavity) via a catheter and may be used to pass dialysate back and forth between the cartridge and the patient's peritoneal cavity by the pump heads during use.

In any event, regardless of the dialysis machine being used and as previously mentioned herein, spent dialysate is transferred to a drain or drain bag. In accordance with one or more aspects of the present disclosure, an improved spent dialysate container for receiving the spent dialysate from the patient is disclosed. In use, the spent dialysate container is arranged and configured to temporarily receive the spent dialysate and to ease transportation and disposal of the spent dialysate to a permanent drain. The spent dialysate container being arranged and configured to provide one or more mechanical advantages to ease disposal of the spent dialysate. For example, the spent dialysate container may be arranged and configured to receive the spent dialysate from the patient's abdomen and enable the patient or caregiver to drain the spent dialysate without requiring the patient or caregiver to lift or carry the bags or incorporate lengthy drain lines.

As previously mentioned, while the spent dialysate container may be used in connection the dialysis machines 150, 200, 300 disclosed herein, it should be appreciated that the spent dialysate container could be used in connection with any dialysis machine now known or hereafter developed. Thus, the spent dialysate container should not be d to any particular type of dialysis machine unless specifically claimed. For example, the system described herein may be incorporated and implemented in connection with other types of and configurations of dialysis machines and medical devices that generate spent dialysate, including hemodialysis machines.

Figure 5:
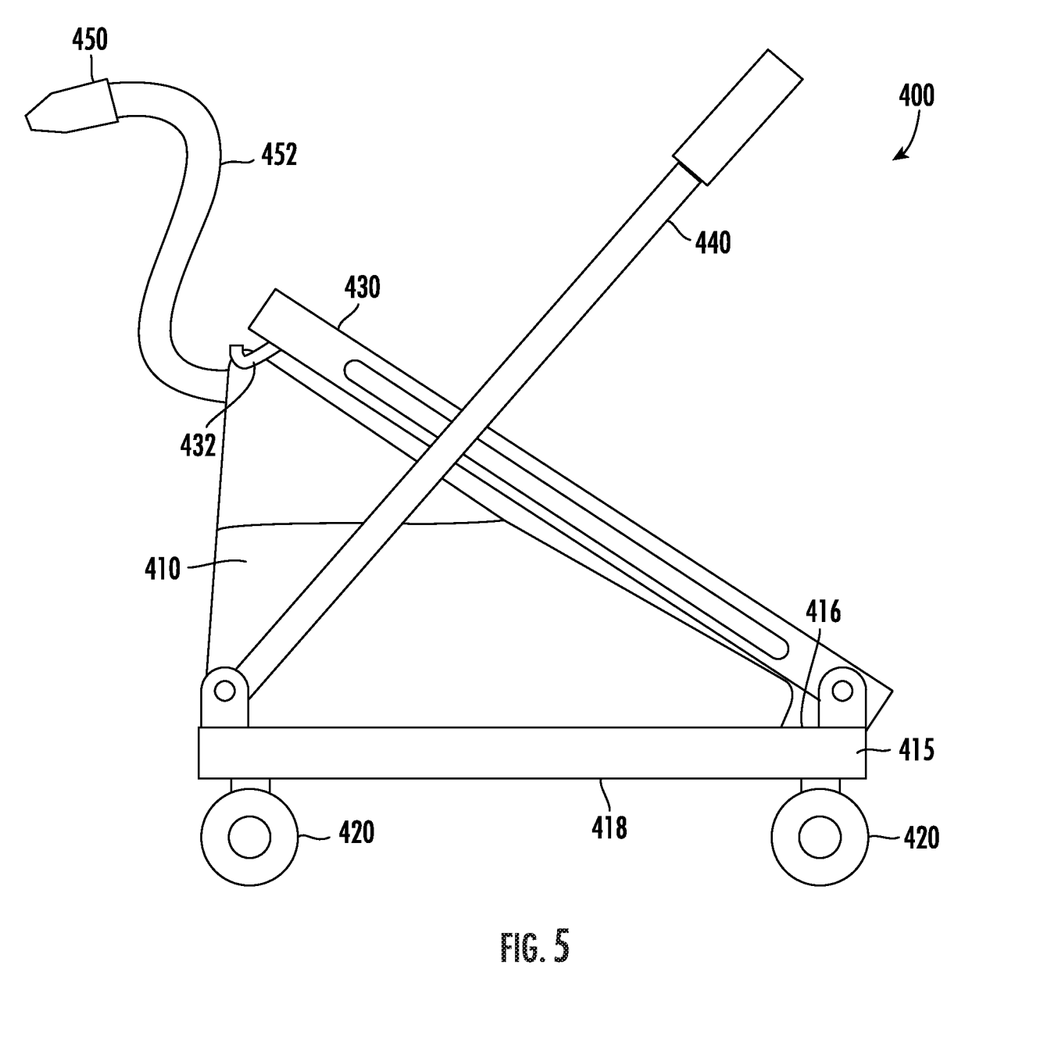
FIG. 5 illustrates an example of an embodiment of a spent dialysate container in accordance with one or more aspects of the present disclosure.

Referring to FIG. 5, an example of an embodiment of a spent dialysate container 400 is illustrated. As illustrated, the spent dialysate container 400 includes a reservoir 410 arranged and configured to receive the spent dialysate from the patient. In one embodiment, the reservoir 410 may be in the form of a non-rigid bag capable of being compressed. The bag may be disposable. In addition, as illustrated, the spent dialysate container 400 may include wheels 420 to enable the patient or caregiver to easily move the spent dialysate container 400, and hence the reservoir 410. As illustrated, in one embodiment, the spent dialysate container 400 may include a base 415 including a top surface 416 and a bottom surface 418. In use, the reservoir 410 may be positioned on the top surface 416 of the base 415. The wheels 420 may extend from the bottom surface 418 of the base 415. In use, at the conclusion of the dialysis treatment, the wheels 420 enable the patient or caregiver to move the spent dialysate container 400 including the spent dialysate stored in the reservoir 410 to facilitate permanent dispose of the spent dialysate without requiring the patient or caregiver to lift, carry, etc. the bags of spent dialysate and/or without the need for lengthy drain tubing.

In addition, the spent dialysate container 400 may also include a mechanism to evacuate the reservoir 410 to facilitate disposal, removal, etc. of the spent dialysate from the reservoir 410. For example, in one embodiment, as illustrate in FIG. 5, the reservoir 410 may be in the form of a disposable, non-rigid bag. The spent dialysate container 400 may include a pan, a basket, or the like disposed on the top surface 416 of the base 415. The spent dialysate container 400 may also include a front or top plate 430. As illustrated, the plate 430 may be pivotably attached to the base 415, although other mechanisms for movably coupling the plate 430 to the base 415 are envisioned. As illustrated, the spent dialysate container 400 may also include a lever 440 arranged and configured to move the plate 430 relative to the base 415, although other mechanisms for moving the plate 430 relative to the base 415 are envisioned. The spent dialysate container 400 may also include a nozzle 450. In one embodiment, the nozzle 450 may be in fluid communication with the reservoir 410 (e.g., non-rigid bag) via, for example, a flexible hose 452 to enable the patient or caregiver to easily direct (e.g., aim) the nozzle 450 towards the permanent drain (e.g., toilet, tub, sink, etc.). In one embodiment, the nozzle 450 may also operate as an inlet for coupling to the drain tubing from the dialysis machine so that the spent dialysate may be received within the reservoir 410. Alternatively, a separate inlet may be provided.

Thus arranged, by positioning the non-rigid bag between the plate 430 and the base 415, a bellows cramp chamber may be provided. For example, in one embodiment, the non-rigid bag may be disposed on the top surface 416 of the base 415 (e.g., on the pan). In addition, the bag may be coupled via, for example, a hook 432 at the top thereof to the plate 430. In use, actuation of the lever 440 to move the plate 430 towards the base 415 compresses or squeezes the reservoir (e.g., non-rigid bag) 410, which in turn causes the volume of spent dialysate received within the reservoir 410 to be discarded from the reservoir 410 through the nozzle 450. At the conclusion, when the spent dialysate is emptied, the patient or caregiver may disconnect the reservoir (e.g., bag) 410 from the spent dialysate container 400 and replace the bag. In this manner, the patient or caregiver can empty the spent dialysate from the bag without having to lift or carry the spent dialysate.

Figure 6:
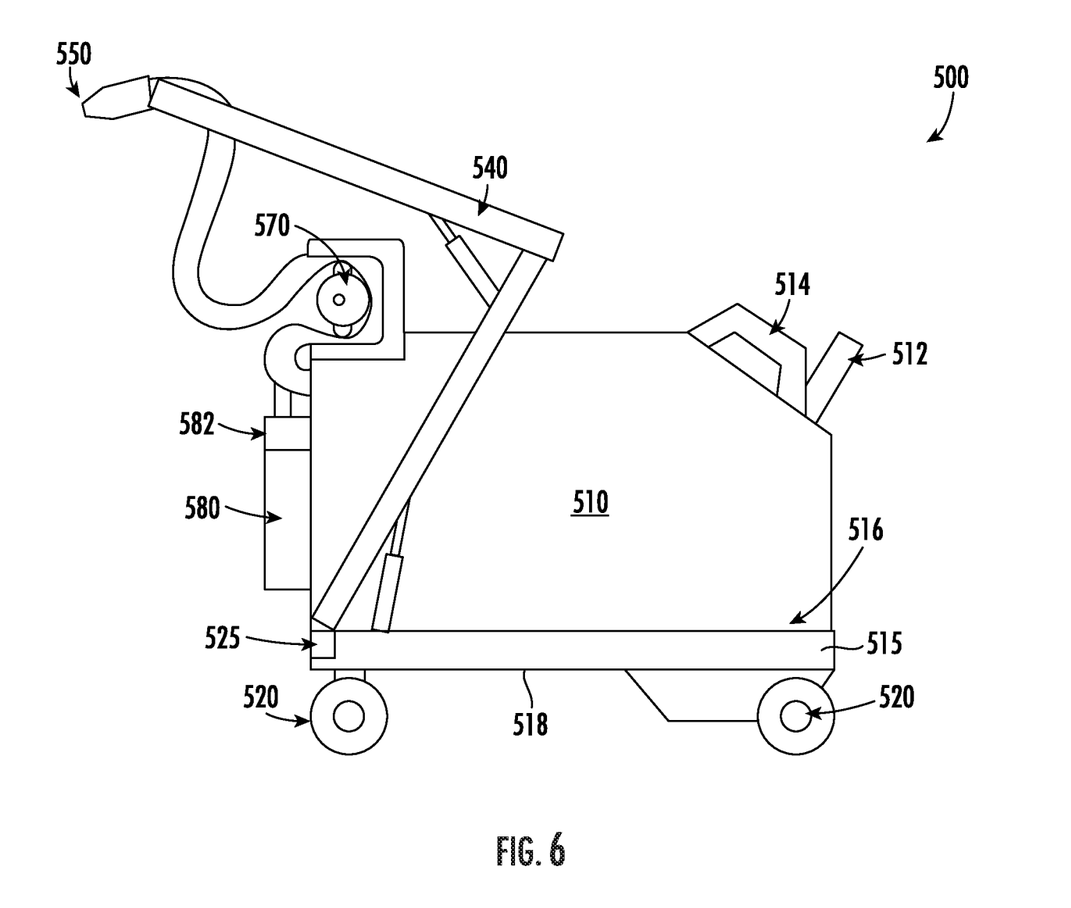
FIG. 6 illustrates an alternate example of an embodiment of a spent dialysate container in accordance with one or more aspects of the present disclosure.

Referring to FIG. 6, an alternate example of an embodiment of a spent dialysate container 500 is illustrated. The spent dialysate container 500 is similar to the spent dialysate container 400 described above, however the spent dialysate container 500 includes one or more features to facilitate improved automation of the dispensing of the spent dialysate. As illustrated, the spent dialysate container 500 includes a reservoir 510 arranged and configured to receive, store, etc. the spent dialysate from the patient. In one embodiment, the reservoir 510 may be in the form of a rigid container to receive, store, etc. the spent dialysate from the patient. Alternatively, the reservoir 510 may be provided in other forms such as, for example, as a non-rigid bag. The bag may be disposable. As illustrated, in one embodiment, the reservoir 510 may include an inlet or port 512 for receiving the drain tube for transferring spent dialysate from the patient to the reservoir 510. In addition, and/or alternatively, the reservoir 510 may include a handle 514 for facilitating guidance of the spent dialysate container 500 for reasons that will become apparent below.

In addition, as illustrated, the spent dialysate container 500 may include a base 515 including a top surface 516 and a bottom surface 518. In use, the reservoir 510 may be positioned on the top surface 516 of the base 515. In addition, wheels 520 may extend from the bottom surface 518 of the base 515. In one embodiment, one or more of the wheels 520 may be motorized to facilitate easier movement of the spent dialysate container 500 including the reservoir 510. In use, at the conclusion of the dialysis treatment, the wheels 520 enable the patient or caregiver to easily move the spent dialysate container 500 including the spent dialysate to facilitate permanent dispose without requiring the patient or caregiver to carry the bags of spent dialysate and/or without the need for lengthy drain tubing.

In one embodiment, the spent dialysate container 500 may also include one or more sensors 525 such as, for example, location or range sensors. In use, the sensors 525 may be arranged and configured to enable the spent dialysate container 500 to self-drive to a designated drain for permanent disposal. Thus arranged, in use the spent dialysate container 500 would eliminate the need for the patient or caregiver to push the spent dialysate container 500 to the permanent drain. For example, in one embodiment, the spent dialysate container 500 may be initially moved from an initial location where the dialysis treatment will be performed to an end location where the spent dialysate will be disposed. The spent dialysate container 500 including the sensors 525 may be arranged and configured to record the route from the initial location to the end location so that, subsequently, the spent dialysate container 500 can travel along the route autonomously. Alternatively, other methods of enabling self-driving of the spent dialysate container 500 are envisioned. For example, in one embodiment, the spent dialysate container 500 may be arranged and configured to map a route using, for example, a computer vision map, and/or be arranged and configured to follow a beacon or token. In use, the patient or caregiver may carry or position the beacon or token at the disposal site. In use, the spent dialysate container 500 may be arranged and configured to follow the beacon or token to the disposal site. In one embodiment, the beacon or token may be in the form of an RFID tag, a Bluetooth transmitter such as, for example, a smartphone, etc. Alternatively, it is envisioned that the spent dialysate container 500 may be wirelessly controlled using, for example, an APP on a smartphone.

In addition, the spent dialysate container 500 may also include a mechanism to facilitate easier dispensing of the spent dialysate from the reservoir 510. For example, in one embodiment, as illustrate in FIG. 6, the spent dialysate container 500 may include a nozzle 550 for dispensing the spent dialysate from the reservoir 510. In addition, the nozzle 550 may be coupled or otherwise operatively associated with an extendable arm 540. The extendable arm 540 may be movable or extendable from a first, folded position (as illustrate in FIG. 6) to a second extended position (not shown). In use, when the spent dialysate container 500 is positioned adjacent to a permanent drain, the extendable arm 540 may be extended to better position the nozzle 550 (e.g., aim) with respect to the permanent drain. In one embodiment, the extendable arm 540 may be coupled to or otherwise associated with a motor, pistons, etc. so that, when the spent dialysate container 500 is positioned adjacent to permanent drain, the extendable arm 540 may be automatically extended. Alternatively, it is envisioned that the extendable arm 540 may be wirelessly controlled using, for example, an APP on a smartphone.

In addition, and/or alternatively, as illustrated, the spent dialysate container 500 may also include a pump 570 to facilitate easier dispensing of the spent dialysate from the reservoir 510. Thus arranged, dispensing the spent dialysate from the reservoir 510 may be automated. That is, for example, in use, with the spent dialysate container 500 position at the permanent drain and with the nozzle 550 properly positioned (e.g., aimed) at the permanent drain, the pump 570 may be activated (e.g., turned on) to dispense the spent dialysate from the reservoir 510 to the permanent drain. In one embodiment, it is envisioned that the pump 570 may be wirelessly activated or controlled using, for example, an APP on a smartphone.

In one embodiment, the pump 570 may be in the form of a peristaltic pump, although any other suitable pump now known or hereafter developed may be utilized. For example, in one embodiment, a single use pump such as, for example, the Quantex Arc pump may be used. In use, the Quantex Arc pump may be integrated into the reservoir or disposable bag. The pump may be coupled to an electric motor. In use, with the spent dialysate container and the nozzle properly positioned, the pump may be activated to dispense the spent dialysate. Thereafter, the reservoir/disposable bag including the pump may be removed and replaced.

In addition, and/or alternatively, referring to FIG. 6, the spent dialysate container 500 may also include a container 580 for storing, for example, a disinfectant such as bleach. The container 580 may also include a valve 582. When emptied, the valve 582 may be opened to dispense the disinfectant from the container 580 to sanitize the permanent drain and the spent dialysate container 500 including, for example, the reservoir 510 and the nozzle 550. In one embodiment, the spent dialysate container 500 may include one or more sensors such as, for example, a pressure sensor or loadcell disposed on, for example, the base 515 to automate determination that the reservoir 510 has been emptied. In one embodiment, it is envisioned that the container 580 and valve 582 may be wirelessly activated or controlled using, for example, an APP on a smartphone.

In addition, in one or more embodiments, the reservoir 410, 510 may include a sensor arranged and configured to determine when the reservoir 410, 510 is approaching maximum capacity. In one embodiment, the reservoir 410, 510 may be configured to trigger an alert when the reservoir 410, 510 is approaching maximum capacity such as, for example, an audible or visible indicator.

Thus arranged, by incorporating one or more features of the spent dialysate container 500, the entire, or at least part of the, disposing process may be automated including, for example, transportation of the spent dialysate via the spent dialysate container from the dialysis treatment site to the permanent drain, positioning of the nozzle relative to the permanent drain, dispensing (e.g., pumping) the spent dialysate from the reservoir to the permanent drain, and/or sanitizing the permanent drain and spent dialysate container with a disinfectant. In addition, in one embodiment, at the conclusion of the dispensing process, the spent dialysate container may be arranged and configured to drive back to the dialysis treatment site to wait for the next treatment.

The spent dialysate containers described herein has been explained in connection with dialysis machines and/or systems having a particular configuration. It is contemplated that the spent dialysate containers described herein may be used with dialysis machines and/or systems having other configurations, for example, different types of dialysis machines and/or dialysis machines having cassettes positionable in other configurations and having other features. The spent dialysate containers described herein may be used with any appropriate dialysis machine and/or system.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The foregoing discussion has been presented for purposes of illustration and description and is not intended to limit the disclosure to the form or forms disclosed herein. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. In addition, while certain embodiments have been described and illustrated with certain features, it is envisioned that features of one embodiment may be used in combination with other embodiments. Moreover, the following claims are hereby incorporated into this Detailed Description by this reference, with each claim standing on its own as a separate embodiment of the present disclosure.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A spent dialysate container, comprising:
   a reservoir arranged and configured to receive spent dialysate resulting from a dialysis treatment;
   wheels arranged and configured to enable the spent dialysate container to move; and
   a pump arranged and configured to evacuate the spent dialysate from the reservoir to facilitate disposal of the spent dialysate; wherein the pump comprises a plate pivotably coupled to a base of the spent dialysate container, the plate movable from a first position to a second position, in the second position, the plate compresses the reservoir causing the spent dialysate to evacuate the reservoir.

2. The spent dialysate container of claim 1, further comprising a lever arranged and configured to move the plate between the first and second positions.

3. The spent dialysate container of claim 1, wherein one or more of the wheels are motorized to facilitate motorized movement of the spent dialysate container.

4. The spent dialysate container of claim 3, wherein the motorized movement of the spent dialysate container is controllable by one or more of (i) controls disposed on the spent dialysate container, or (ii) a remote controller.

5. The spent dialysate container of claim 1, further comprising one or more sensors arranged and configured to enable the spent dialysate container to autonomously move to a designated drain for permanent disposal of the spent dialysate.

6. The spent dialysate container of claim 1, further comprising:
   a flexible hose and a nozzle at an end thereof for evacuating the spent dialysate from the reservoir; and
   an extendable arm operatively coupled to the nozzle, the extendable arm movable between a first, folded position and a second extended position, in the second position, the extendable arm facilitating placement of the nozzle relative to a drain.

7. The spent dialysate container of claim 6, further comprising a motor for moving the extendable arm between the first and second positions, wherein the motor is arranged and configured to automatically move the extendable arm from the first position to the second position when one or more sensors detect that the spent dialysate container is positioned adjacent to the drain.

8. The spent dialysate container of claim 1, wherein the pump is arranged and configured to automatically evacuate the spent dialysate when one or more sensors detect that the spent dialysate container is positioned adjacent to the drain.

9. The spent dialysate container of claim 1, wherein the spent dialysate container further comprises a container for storing a disinfectant and a valve, the valve configurable between an opened position and a closed position, in the opened position, the container releasing disinfectant to clean a drain, the reservoir, or a combination thereof.

10. A dialysis system for conducting a dialysis treatment, comprising:
    a dialysate source for use in the dialysis treatment;
    a dialysis machine for transferring dialysate from the dialysate source during the dialysis treatment; and
    a spent dialysate container for receiving spent dialysate resulting from the dialysis treatment via the dialysis machine, the spent dialysate container including:
      a reservoir arranged and configured to receive the spent dialysate;
      wheels arranged and configured to enable the spent dialysate container to move;
      a pump arranged and configured to evacuate the spent dialysate from the reservoir to facilitate disposal of the spent dialysate; and
      a plate pivotably coupled to a base of the spent dialysate container, the plate movable from a first position to a second position, in the second position, the plate compresses the reservoir causing the spent dialysate to evacuate the reservoir.

11. The dialysis system of claim 10, wherein the spent dialysate container further comprises a lever arranged and configured to move the plate between the first and second positions.

12. The dialysis system of claim 10, wherein one or more of the wheels are motorized to facilitate motorized movement of the spent dialysate container.

13. The dialysis system of claim 12, wherein the movement of the spent dialysate container is controllable by one or more of (i) controls disposed on the spent dialysate container, or (ii) a remote controller.

14. The dialysis system of claim 12, wherein the spent dialysate container includes one or more sensors arranged and configured to enable the spent dialysate container to autonomously move to a designated drain for permanent disposal of the spent dialysate.

15. The dialysis system of claim 10, wherein the pump is arranged and configured to automatically evacuate the spent dialysate when one or more sensors detect that the spent dialysate container is positioned adjacent to the drain.

16. The dialysis system of claim 10, wherein the spent dialysate container further comprises a container for storing a disinfectant and a valve, the valve configurable between an opened position and a closed position, in the opened position, the container releasing disinfectant to clean a drain, the reservoir, or a combination thereof.

17. A dialysis system for conducting a dialysis treatment, comprising:
    a dialysate source for use in the dialysis treatment;
    a dialysis machine for transferring dialysate from the dialysate source during the dialysis treatment; and
    a spent dialysate container for receiving spent dialysate resulting from the dialysis treatment via the dialysis machine, the spent dialysate container including:
      a reservoir arranged and configured to receive the spent dialysate;
      wheels arranged and configured to enable the spent dialysate container to move;

a pump arranged and configured to evacuate the spent dialysate from the reservoir to facilitate disposal of the spent dialysate; and a flexible hose and a nozzle at an end thereof for evacuating the spent dialysate from the reservoir, the spent dialysate container further including an extendable arm operatively coupled to the nozzle, the extendable arm movable between a first, folded position and a second extended position, in the second position, the extendable arm facilitating placement of the nozzle relative to a drain.

18. The dialysis system of claim 17, wherein the spent dialysate container further comprises a motor for moving the extendable arm between the first and second positions, wherein the motor is arranged and configured to automatically move the extendable arm from the first position to the second position when one or more sensors detect that the spent dialysate container is positioned adjacent to the drain.

19. A spent dialysate container, comprising:
- a reservoir arranged and configured to receive spent dialysate resulting from a dialysis treatment;
- wheels arranged and configured to enable the spent dialysate container to move;
- a pump arranged and configured to evacuate the spent dialysate from the reservoir to facilitate disposal of the spent dialysate;
- a flexible hose and a nozzle at an end thereof for evacuating the spent dialysate from the reservoir; and
- an extendable arm operatively coupled to the nozzle, the extendable arm movable between a first, folded position and a second extended position, in the second position, the extendable arm facilitating placement of the nozzle relative to a drain.

20. The spent dialysate container of claim 19, wherein one or more of the wheels are motorized to facilitate motorized movement of the spent dialysate container.

21. The spent dialysate container of claim 20, wherein the motorized movement of the spent dialysate container is controllable by one or more of (i) controls disposed on the spent dialysate container, or (ii) a remote controller.

22. The spent dialysate container of claim 20, further comprising one or more sensors arranged and configured to enable the spent dialysate container to autonomously move to a designated drain for permanent disposal of the spent dialysate.

23. The spent dialysate container of claim 19, further comprising a motor for moving the extendable arm between the first and second positions, wherein the motor is arranged and configured to automatically move the extendable arm from the first position to the second position when one or more sensors detect that the spent dialysate container is positioned adjacent to the drain.

24. The spent dialysate container of claim 19, wherein the pump is arranged and configured to automatically evacuate the spent dialysate when one or more sensors detect that the spent dialysate container is positioned adjacent to the drain.

25. The spent dialysate container of claim 19, wherein the spent dialysate container further comprises a container for storing a disinfectant and a valve, the valve configurable between an opened position and a closed position, in the opened position, the container releasing disinfectant to clean a drain, the reservoir, or a combination thereof.

* * * * *